(12) United States Patent
Saragovi et al.

(10) Patent No.: US 6,610,500 B1
(45) Date of Patent: Aug. 26, 2003

(54) DESIGN OF HORMONE-LIKE ANTIBODIES WITH AGONISTIC AND ANTAGONISTIC FUNCTIONS

(75) Inventors: H. Uri Saragovi, Westmount (CA); Lynne LeSauteur, Rosemère (CA)

(73) Assignee: McGill University, Montreal (CA)

( * ) Notice: Subject to any disclaimer, the term of this patent is extended or adjusted under 35 U.S.C. 154(b) by 0 days.

(21) Appl. No.: 09/091,071

(22) PCT Filed: Dec. 6, 1996

(86) PCT No.: PCT/CA96/00815
§ 371 (c)(1),
(2), (4) Date: Jun. 8, 1998

(87) PCT Pub. No.: WO97/21732
PCT Pub. Date: Jun. 19, 1997

(30) Foreign Application Priority Data

Dec. 8, 1995 (GB) .............................. 9525180

(51) Int. Cl.⁷ .............................. G01N 33/53
(52) U.S. Cl. ............ 435/7.2; 435/7.1; 530/387.1; 530/388.1; 530/388.2; 424/130.1
(58) Field of Search ............ 530/387.1, 388.1, 530/388.22; 435/7.1, 7.2; 424/130.1

(56) References Cited

U.S. PATENT DOCUMENTS 5,753,225 A * 5/1998 Clary et al. .............. 424/130.1

FOREIGN PATENT DOCUMENTS

| EP | 0 388 914 A | 9/1990 |
| WO | WO 95/15180 | 6/1995 |

OTHER PUBLICATIONS

1/ Eager, KB. Oncogene 6(5) : 819–824, 1991.*
2/ Clary, DO et al. Mol. Biol. Cell 5 : 549–563, 1994.*
3/Martin–Zanca et al, Mol. Cell Biol. 9: 24–33, 1989.*
4/ Meakin SO et al, Accession No.357, 739 GenBank/ MPSKCH Search, 1992.*
5/ Meakin SO et al, PNAS, USA, 89: 2374–2378, 1992.*
6/ Perez, P et al. Mol. Cell NeuroSci. 6 : 97–105, 1995.*
7/ Tynan RE et al. Neuron, 14: 755–862, 1995.*
8/ Gillies, SD. J. Immunol. 146 (3) : 1067–71, 1991.*
9/ Bauki et al. JBL. 269 : 2847–2851, 1994.*
Bogenmann, E. et al. (1995) *Oncogene*, 10: 1915–1925.
Clary, D.O. et al. (1994) *Mol. Biol. Cell.*, 5: 549–563.
Hansen, M.B. et al. (1989) *Jour. Immunol. Meth.*, 119: 203–210.
Harlow, E., Lane D. (1988) *A Laboratory Manual*. Cold Spring Harbour Laboratory Publishing. Chapter 9:332–333.
Hsu, S–M. et al. (1981) *J. Histochem. Cytochem.*, 29: 577–580.
Jing, S. et al. (1992) *Neuron*, 9: 1067–1079.
Kaplan, D.R. et al. (1994) *J. Neurobiol.*, 25: 1404–1417.
LeSauteur, L. et al.(1995) *J. Biol. Chem.*, 270:6564–6569.
Perez, P. et al. (1995) *Mol. Cell. Neurosc.*, 6: 97–105.
Sargovi, H.U. et al. (1991) *Science*, 253: 792–795.
Sibanda, B.L. et al. (1989) *J. Mol. Biol.*, 206: 759–777.
Taub, R. et al. (1992) *Biochemistry*, 31: 7431–7435.
Twyman, R.E. et al. (1995) *Neuron*, 14: 755–762.
Kramer K. et al. (1995) *Proceedings of the American Association for Cancer Research*, 36:24–.
Hempstead B. et al. (1991), *Nature*, 350:678–683.
McDonald P. et al. (1995), *European Journal of Immunology*, 25:2870–2876.
LeSauteur, L. et al.(1996) *The Journal of Neuroscience*, 16:1308–1316.
Kramer K. et al., (1996), *Clinical Cancer Research*, 2:1361–1367.
LeSauteur, L. et al.(1996) *Nature Biotechnology*, 14:1120–1122.

* cited by examiner

*Primary Examiner*—Susan Ungar
*Assistant Examiner*—Minh-Tam Davis
(74) *Attorney, Agent, or Firm*—Klauber & Jackson

(57) ABSTRACT

The present invention relates to an agonistic anti-human TrkA mAb 5C3 which recognizes the NGF docking site. Such antibodies may be used for the treatment, diagnosis or prevention of neurological diseases, neuromas and neoplastic tumors which express TrkA receptors. Also these antibodies may be used to develop and screen for pharmaceutical agents which are agonistic or antagonistic to NGF binding to the TrkA receptors.

5 Claims, 11 Drawing Sheets

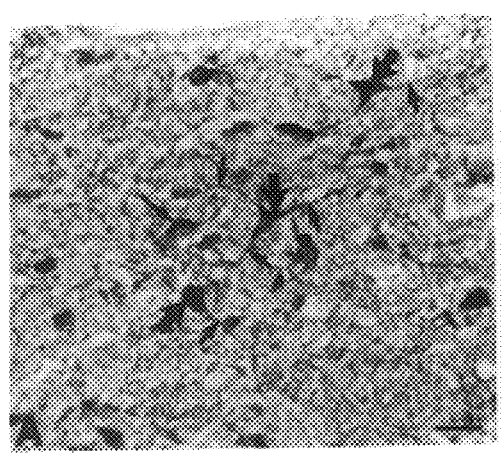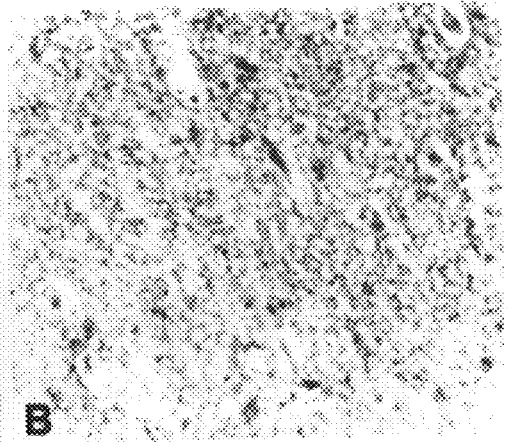
FIG. 3A  FIG. 3B

FIG. 3C  FIG. 3D  FIG. 3E
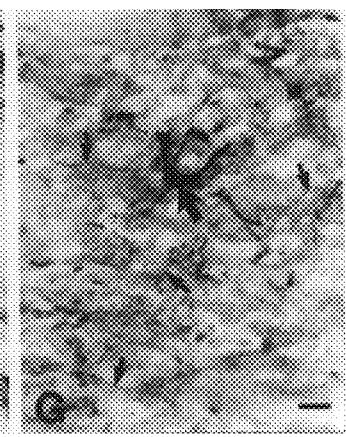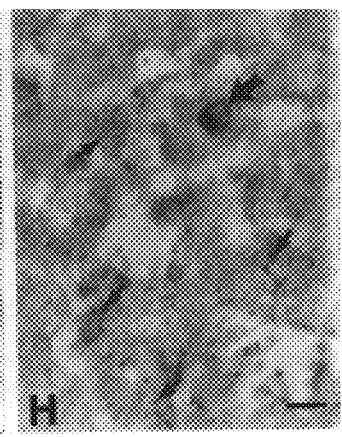
FIG. 3F  FIG. 3G  FIG. 3H

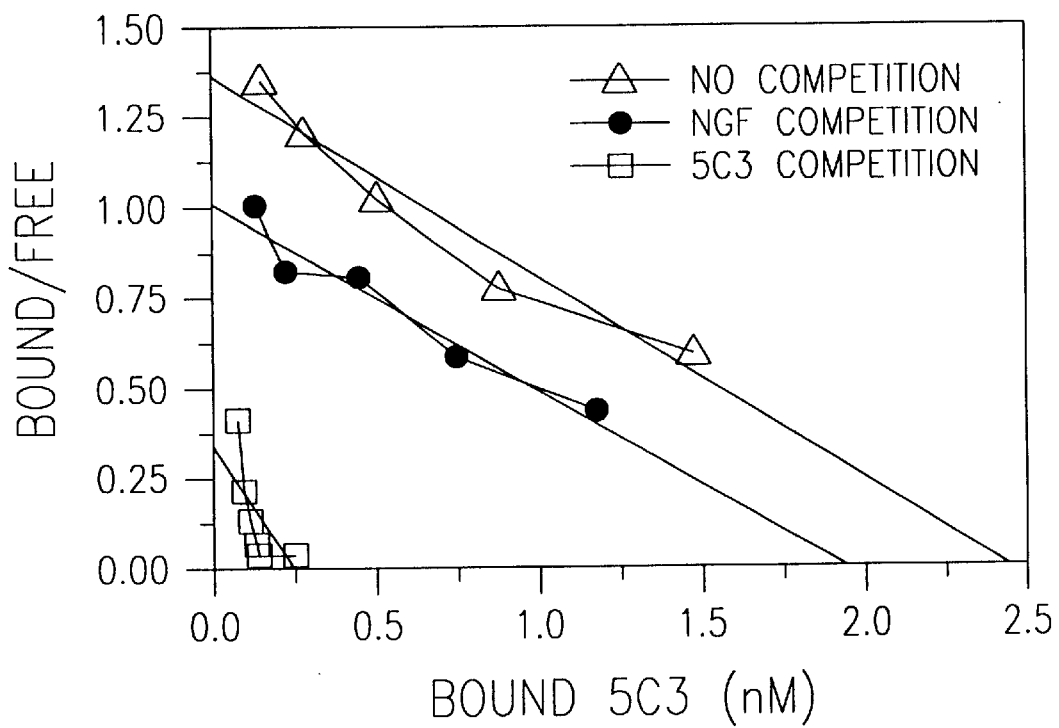
FIG_4

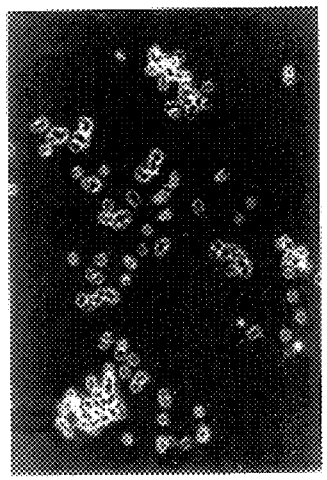
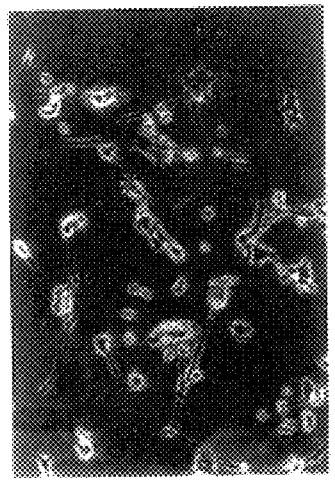
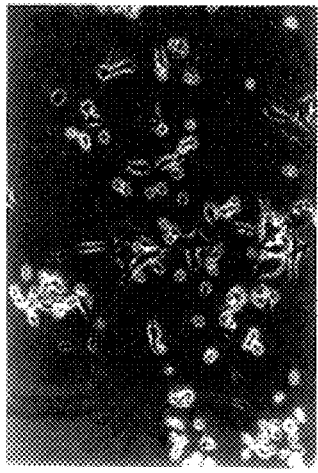
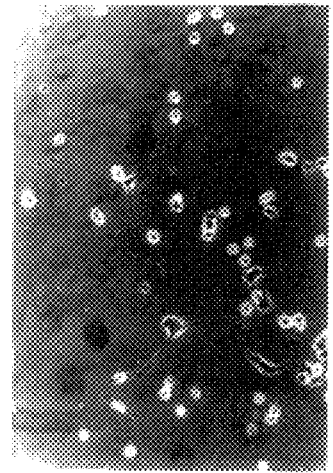
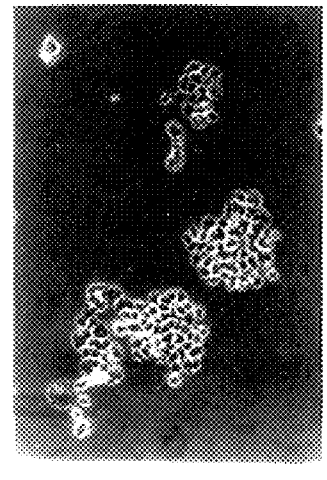
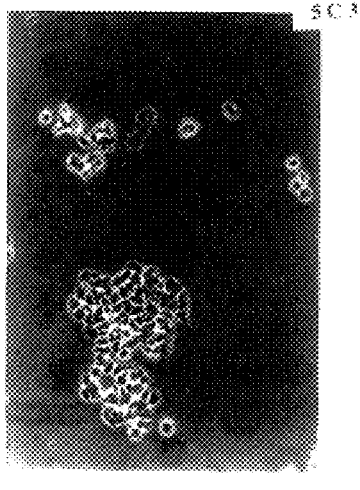
FIG. 9

Mab 5C3 prevents TrkA-Expressing Tumor growth *in vivo*

| TREATMENT (3*100ug I.P.) | MOUSE WEIGHT (g) | PRIMARY TUMOR WEIGHT (mg) | METASTIC TUMOR WEIGHT (mg) |
|---|---|---|---|
| 5C3 | 37.4 <br> 35.8 | 50 (fibrotic) | none |
| mIgG | 39.1 <br> 39.2 | 1200 <br> 400 | 400 <br> 300 |

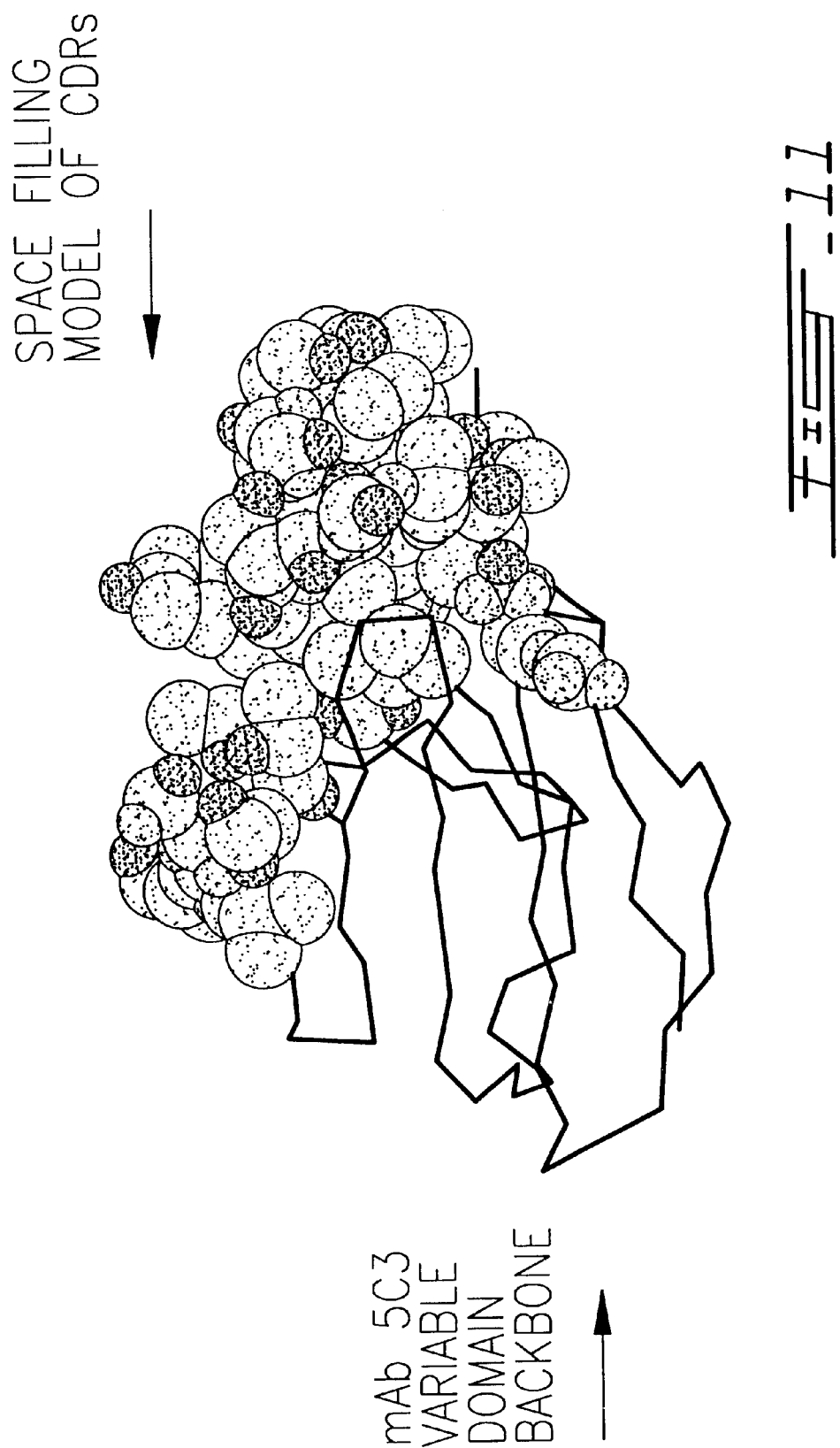

DESIGN OF HORMONE-LIKE ANTIBODIES WITH AGONISTIC AND ANTAGONISTIC FUNCTIONS

This application is the 35 U.S.C. §371 National Phase of PCT/CA96/00815, filed Dec. 6, 1996, which claims priority of GB 9525180.7, filed Dec. 8, 1995.

BACKGROUND OF THE INVENTION (a) Field of the Invention

The invention relates to a method of designing agonistic and/or antagonistic antibodies for any hormone receptor more specifically antibodies which are capable of blocking nerve growth factor (NGF) binding and antibodies which can mimic NGF binding to its receptor.

(b) Description of Prior Art

The TrkA receptor is a 140 kDa transmembrane glycoprotein with tyrosine kinase activity that functions as the Nerve Growth Factor (NGF) receptor. NGF also binds with low affinity to a p75 receptor whose signaling function is unclear. Homo or heterodimers or oligomers of TrkA and p75 bind NGF with higher affinity (Jing, S. et al. (1992) *Neuron*, 9: 1067–1079) suggesting that specific receptor conformations may play specific functions.

NGF promotes the differentiation of certain neuronal cells, is mitogenic for TrkA-transfected fibroblasts, and allows survival in serum-deprived conditions for both cell types. Activation of the tyrosine kinase activity of TrkA via UGF binding leads to receptor trans- and auto-tyrosine phosphorylation (PY), and PY of second messengers including phosphatidylinositol-3 kinase (PI-3 kinase). PI-3 kinase is involved in protein trafficking and endocytosis of ligand-receptor complexes (reviewed by Kaplan, D. R. et al. (1994) *J. Neurobiol.*, 25: 1404–1417). Since microinjection of NGF into cells does not result in NGF biological signals, cell surface receptor ligation and internalization of TrkA or NGF-TrkA complexes must mediate these effects.

TrkA, like most kinase growth factor receptors, signals through receptor oligomerization. Thus, mono-valent TrkA-binding agents are antagonistic or have no biological effects (LeSauteur, L. et al.(1995) *J. Biol. Chem.*, 270:6564–6569), whereas bivalent receptor-binding agents such as NGF (a homodimer) or antibodies can be agonistic. The principle of using polyclonal antibodies to activate neural receptors has been demonstrated (Twyman, R. E. et al. (1995) *Neuron*, 14: 755–762). In contrast, only a limited number of anti-receptor monoclonal antibodies (mAb) mimic ligand functions (Taub, R. et al. (1992) *Biochemistry*, 31: 7431–7435), and none exist against neurotrophin receptors.

It would be highly desirable to be provided with an agonistic or antagonistic anti-human TrkA mAb which recognizes the NGF docking site. Such antibodies may be used for the diagnosis, treatment or prevention of neurological diseases, neuromas and neoplastic tumors which express TrkA receptors. Also these antibodies may be used to develop and screen for pharmaceutical agents which are agonistic or antagonistic by binding to the TrkA receptors.

SUMMARY OF THE INVENTION

One aim of the present invention is to report the development and characterization of an agonistic anti-human TrkA mAb 5C3 which recognizes at least one NGF docking site. This MAb 5C3 was used to characterize the pattern of TrkA protein expression in normal human brain, and the NGF binding features of the receptor. MAb 5C3 behaves like NGF in bioassays, and monomeric 5C3 $F_{abs}$ retained binding and functional agonistic activity. MAb 5C3 will be useful to identify the NGF docking site on TrkA and possibly as a pharmacological lead in the development of small mimetics.

In accordance with the present invention there is provided an antibody or functional fragment thereof which binds to at least the TrkA receptor under physiological conditions, and wherein the binding to the receptor at least partially mimics or inhibits nerve growth factor biological activity.

In accordance with the present invention there is also provided a method of screening pharmacological agents which are capable to mimic or inhibit nerve growth factor biological activity, which comprises using the antibody of the present invention to screen for pharmacological agents capable of binding to the complementary determining region of the antibody, wherein the screened pharmacological agents can mimic or inhibit nerve growth factor biological activity.

In accordance with the present invention there is also provided the use of pharmacological agents obtained by the process of the present invention, for the in vivo inhibition of nerve growth factor binding to TrkA receptor or the internalization or downmodulation of the receptor.

In accordance with the present invention there is also provided the use of the antibody of the present invention, for the in vivo inhibition of nerve growth factor binding to TrkA receptor or the internalization or downmodulation of the receptor, such as for inhibiting tumor growth in situ, for the treatment or prevention of neurological diseases, neuromas and neoplastic tumors which express TrkA receptors, for mapping hormone-receptor interactive sites and receptor domain-function correlation such as mapping TrkA docking sites, for screening pharmacological agents which bind to the hormone-receptor interactive sites.

In accordance with the present invention there is also provided an antibody having CDR-like domains of hormones, wherein the antibody or functional fragment thereof binds to at least TrkA receptor under physiological conditions, and wherein the binding to the receptor at least partially mimics or inhibits nerve growth factor biological activity.

In accordance with the present invention there is also provided a method for the treatment of neurological diseases, neuromas and neoplastic tumors which express TrkA receptors in a patient, which comprises administering an effective amount of an antibody of the present invention or a functional fragment thereof to a patient.

In accordance with the present invention there is also provided a pharmaceutical composition for the treatment of neurological diseases, neuromas and neoplastic tumors which express TrkA receptors, which comprises an effective amount of an antibody of the present invention or a functional fragment thereof in association with a pharmaceutically acceptable carrier.

In accordance with the present invention there is also provided a method for immunization of a mammal against an antibody of the present invention or a functional fragment thereof, which comprises administering by systemic injection an immunizing amount of at least one of the antibody or the fragment thereof in an immunogenic form in association with a pharmaceutically acceptable carrier.

In accordance with the present invention there is also provided a method for the prognosis or diagnosis of human tumors which comprises:

a) biopsy and immunocytochemistry of tumors using the antibody of the present invention and fragments thereof; or b) radiolabeling of the antibody of the present invention and fragments thereof and nuclear imaging analysis.

In accordance with the present invention there is also provided a method for the treatment of human tumor of a patient which comprises the steps of:

a) coupling cytotoxic agents to the antibody of the present invention and fragments thereof;

b) administering the coupled antibody of step a) to the patient.

In accordance with the present invention there is also provided a pharmaceutical composition for the targeting of pharmaceutical agents to tissues of the central and/or peripheral nervous system, which comprises an effective amount of an antibody of the present invention or a functional fragment thereof coupled to a pharmaceutical agent in association with a pharmaceutically acceptable carrier. The pharmaceutical agent may be selected from the group consisting of radioligands, nucleic acid molecules, toxins, growth factors and gangliosides.

In accordance with the present invention there is also provided a TrkA docking site which binds to the antibody of the present invention.

In accordance with the present invention there is also provided the use of the docking site of the present invention for screening pharmacological agents which are capable to mimic or inhibit nerve growth factor biological activity and said antibody biological antibody.

BRIEF DESCRIPTION OF THE DRAWINGS

FIG. 3 (FIGS. 3A, 3B, 3C, 3D, 3E, 3F, 3G, 3H) illustrates TrkA immunoreactivity in normal human brain;

FIG. 4 illustrates the induction of TrkA-tyrosine phosphorylation by 5C3;

FIG. 9 illustrates the differentiation/neurito-genesis of human TrkA-expressing cells in serum media;

FIG. 11 illustrates the topography of the CDRs of the present invention.

DETAILED DESCRIPTION OF THE INVENTION

Figure 1A:
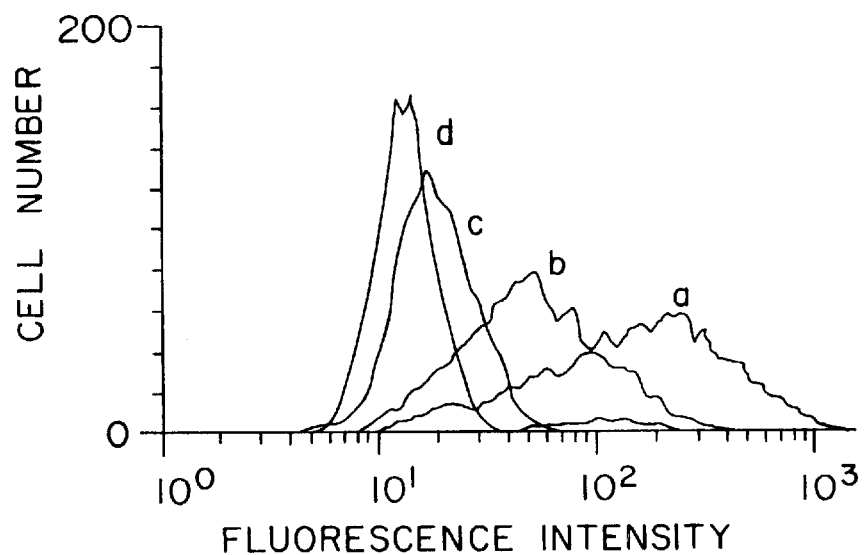
FIG. 1 (FIG. 1A, FIG. 1B) illustrates surface immunofluorescence studies with mAb 5C3.

Monoclonal antibody (mAb) 5C3 directed against human p140 TrkA is a structural and functional mimic of NGF and an artificial receptor agonist. MAb 5C3 binds in the Nerve Growth Factor (NGF) docking site, and like NGF it promotes TrkA internalization; TrkA and phosphatidylinositol-3 kinase tyrosine phosphorylation; and increased transformation of TrkA-expressing fibroblasts. More importantly, mAb 5C3 protects human TrkA-expressing cells from apoptotic death in serum-free media. Interestingly, agonistic activity is observed with monomeric $F_{ab}$ 5C3 fragments. The affinity of mAb 5C3 is ~2 nM and was used to study features of ligand binding by TrkA and the distribution of TrkA protein in normal human brain.

Antibodies

Female Balb/c mice were immunized with human TrkA, and splenocytes fused to SP2/0 myelomas. Hybridomas were screened by differential binding between untransfected and TrkA-transfected cells using a Fluorescent Activated Cell Scanner™ (FACScan) (Becton Dickinson, Calif.). MAb 5C3 was identified and subcloned 3 times. Rat anti-mouse IgG (amIgG) (Sigma, Saint Louis, Mo.), anti-phosphotyrosine mAb 4G10 (UBI, Lake Placid, N.Y.), and anti-PI-3 kinase polyclonal serum (UBI) were purchased, mouse anti-rat p75 mAb MC192 ascites were a gift from P. Barker, and anti-p65 mAb 87.92.6 was grown in the laboratory.

Monomeric mAb 5C3 $F_{abs}$

MAb 5C3 was purified (1 mg/ml) with Protein G-Sepharose™ (Sigma) and digested with papain (10 μg/ml) (GIBCO, Toronto, Ontario). $F_{abs}$ were repurified on KappaLock-Sepharose™ (UBI) and Protein G-Sepharose™ and dialyzed against phosphate buffered saline (PBS). All products were characterized by SDS-PAGE under non-reducing or reducing conditions (100 mM 2-mercaptoethanol) to >98% purity. Control $F_{abs}$ from anti-rat p75 mAb MC192 were similarly prepared.

Cell Lines

Mouse SP2/0 myelomas, mouse R1.1 and EL4 thymomas, mouse NIH-3T3 fibroblasts, mouse 2B4 T cell hybridomas, NGF responsive-rat PC12 pheochromocytoma cells, human Jurkat T lymphomas, and human HeLa fibroblasts were used. NIH-3T3 cells transfected either with human p140trkA cDNA (E25 cells), with p75 cDNA (Z91 cells), or p75 and p140tzkA cDNAs (R7 cells) (Jing, S. et al. (1992) *Neuron*, 9: 1067–1079). The trk negative rat B104 neuronal cell line (expressing endogenous rat p75), and B104 transfected with human trkA CDNA (4–3.6 cells, expressing human TrkA and rat p75) were kindly provided by Dr. E. Bogenmann (Bogenmann, E. et al. (1995) *Oncogene*, 10: 1915–1925). PC12 cells transfected with human trkA CDNA were obtained from Dr. Kaplan. All cells were cultured in RPMI media supplemented with 5–10% Fetal Bovine Serum (FBS) and antibiotics (GIBCO). Transfectants were added the appropriate drug selection.

FACScan $5 \times 10^5$ cells in 0.1 ml of binding buffer (Hanks' Balanced Salt Solution (HBSS), 0.1% BSA, 0.1% $NaN_3$) were incubated with the indicated concentration of mabs or $F_{abs}$ for 30 min at 4° C., washed in binding buffer to remove excess primary antibody, and immunostained with fluorescinated (FITC) goat anti-mouse IgG (FITC-GαmIgG), or anti-mouse Fab (FITC-GαmF$_{ab}$) (Sigma) secondary antibody for 30 min at 4° C. Cells were acquired and analyzed on a FACScan (Becton Dickinson, Calif.) using the LYSIS II™ program. As negative controls (background fluorescence) either mouse IgG (Sigma), mAb 192 or 192 $F_{abs}$ were used as primary, followed by appropriate secondary.

Characterization of mAb 5C3

FACScan analysis of non-permeabilized cells demonstrated that mAb 5C3 recognizes the extracellular domain of human TrkA receptors (Table 1, FIG. 1A).

TABLE 1

Surface phenotyping with mAb 5C3

| CELLS | 5C3 BINDING |
|---|---|
| E25 (hTrkA) | +++++ |
| R7 (hTrkA/p75) | +++ |
| Z91 (p75) | − |
| 4-3.6 (hTrkA/p75) | +++ |
| B104 (p75) | − |
| PC12 (rTrkA/p75) | − |
| transient NIH-3T3 transfections | |
| htrkA cDNA | ++ |
| htrkB cDNA | − |
| rtrkB cDNA | − |
| rtrkA cDNA | − |

The indicated cell lines expressing human TrkA (hTrkA), rat TrkA (rTrkA) and/or p75 were analyzed by surface immunofluorocytometry with mAb 5C3 versus control mIgG. Transient transfections (48 hrs) were done by electroporation of cDNAs. Relative intensities of staining are indicated as +++++ (high staining) or − (no staining) (see FIG. 1). Saturating doses of mAb were used, and differences represent receptor number. Other cells tested include wild type NIH-3T3, Jurkat, R1.1, EL4, 2B4, and HeLa cells which are all negative.

Human TrkA-transfectant lines 4-3.6, E25, and R7, bound mAb 5C3. In contrast, rat PC12 (expressing rat TrkA and rat p75), rat B104 (parental cells of 4-3.6, expressing rat p75), Z91 (NIH-3T3 transfected with p75), wild type NIH-3T3, or NIH-3T3 cells transiently transfected with human trkB, rat trkA, or rat trkB cDNA did not bind mAb 5C3. Thus, mAb 5C3 is specific for human TrkA, and co-expression of rat or human p75 does not interfere with binding.

Figure 1B:
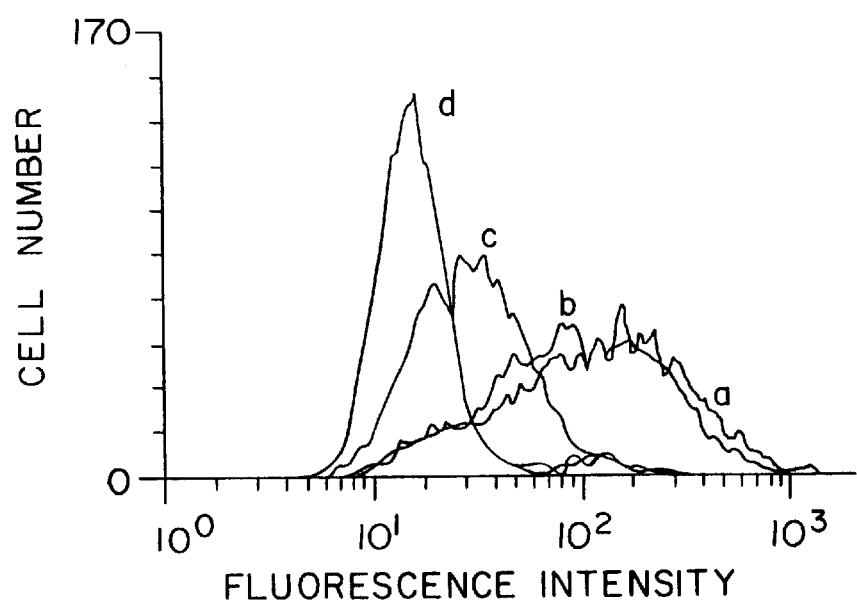

The concentration of mAb 5C3 required to saturate TrkA receptors was determined in E25 cells by testing increasing amounts of antibody in FACScan assays (FIG. 1A). Similar analysis with mAb 5C3 $F_{abs}$ demonstrated that specificity and saturability were similar to that obtained with intact mAb but that 3-fold lower $F_{ab}$ protein concentrations were required (FIG. 1B). Since the molecular weight of 5C3 $F_{ab}$ is 3-fold lower than 5C3 IgG (~50 versus ~150 kDa), equimolar concentrations were required for saturation.

E25 cells expressing human TrkA were analyzed by indirect immunofluorescence in a FACScan with various doses of mAb 5C3 or 5C3 $F_{abs}$ to assess ligand concentrations that achieve receptor saturation.

(FIG. 1A) mAb 5C3 doses: 0.02 μg/ml (thick line, c); 0.2 μg/ml (thin line, b); 2 μg/ml (dotted line, a). For background fluorescence mIgG at 2 μg/ml (crossed line, d) was used. (FIG. 1B) 5C3 $F_{abs}$ doses: 0.007 μg/ml (thick line, c); 0.07 μg/ml (thin line, b); 0.7 μg/ml (dotted line, a). For background fluorescence 192 $F_{ab}$ at 0.7 μg/ml (crossed line, d) was used. Increased fluorescence intensity (X axis of histograms) reflect increased staining by mAb 5C3 or 5C3 $F_{abs}$. The areas under the curves represent the total number of cells acquired for each sample (constant 5000 cells). Histogram heterogeneity is due to individual cell receptor density.

Figure 2A:
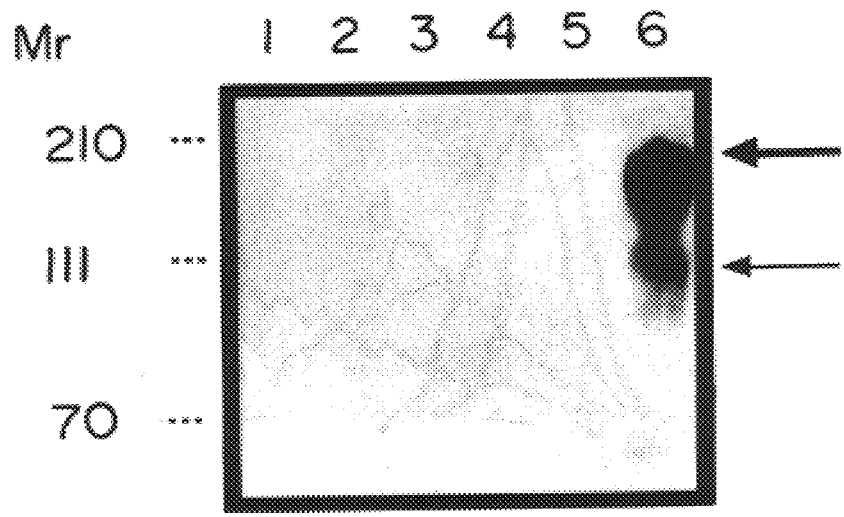
FIG. 2 (FIG. 2A, FIG. 2B) illustrates the direct detection of p140 TrkA by western blotting.
Figure 2B:
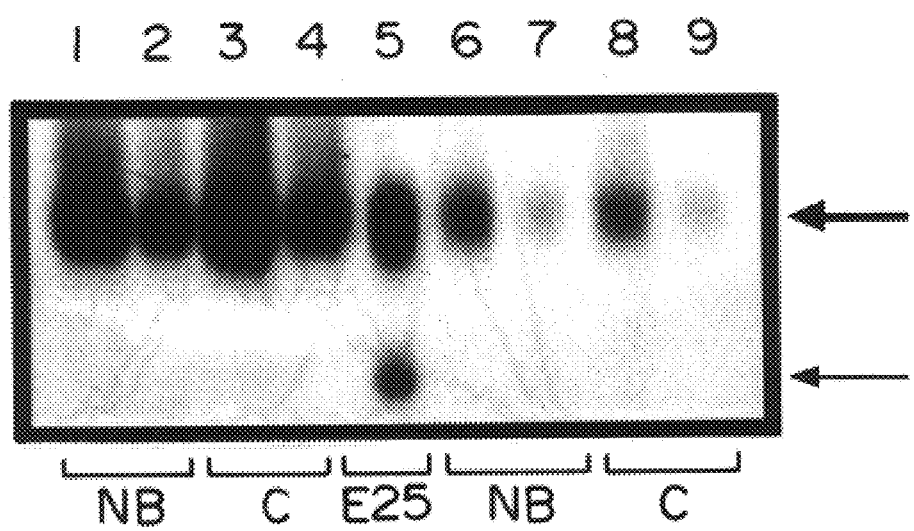

Western blot analysis with mAb 5C3 revealed heterogeneous material of $M_r$ 140,000 (p140) for samples from E25 and 4-3.6 cells, but not for control cells (FIG. 2A). In these cells a band of ~110 kDa (p110) was also observed, previously thought to be intracellular TrkA precursors. The p140 band was also immunoblotted in samples dissected from normal human cortex or nucleus basalis of Meynert (FIG. 2B). The 110 band was not seen perhaps due to different post-translational processing in neuronal tissues with respect to transfected cell lines. MAb 5C3 was effective in western blot analysis only when samples were prepared under non-reducing or mildly reducing conditions, indicating that a disulfide bond-stabilized conformational epitope is recognized.

Whole cell detergent lysates ($2 \times 10^6$ cell equivalents/lane) were resolved by SDS-PAGE under non-reducing conditions and analyzed by western blotting with mAb 5C3. (FIG. 2A) Lane 1, Jurkat; lane 2, PC12; lane 3, NIH-3T3; lane 4, R1.1; lane 5, Z91; lane 6, E25. Thick arrow, p140 TrkA; thin arrow, p110. (FIG. 2B) Dissected human brain tissues: nucleus basalis (NB; lanes 1, 2, 6, 7), and cortex (FIG. 2C; lanes 3, 4, 8, 9) were compared to E25 cells (lane 5; $2 \times 10^5$ cell equivalents). Lanes 1 and 3, 300 μg/lane; lanes 2 and 4, 150 μg/lane; lanes 6 and 8, 75 μg/lane; lanes 7 and 9, 33 μg/lane. Thick arrow, p140 TrkA; thin arrow, p110. Note that p110 is not seen in the human brain tissues.

Biochemical Analysis

Cell Lysates $33 \times 10^6$ cells/ml were detergent solubilized (lysis buffer 2% NP-40™, 150 mM NaCl, 50 mM Tris-Glycine, 10 mM NaF, 50 μM $Na_3VO_4$, 30 mM Na Pyrophosphate 10 mM benzamidine, 20 mM iodoacetamide, pH 7.8) supplemented with protease inhibitors (2 μg/ml soybean trypsin inhibitor, 10 μg/ml aprotinin, 5 mM PMSF, and 10 μg/ml leupeptin) for 30 min at 4° C., followed by a 15 minute centrifugation at 14,000 g. Cleared supernatants were analyzed by SDS-PAGE directly (whole cell lysates) or after immunoprecipitation.

Gel Analysis

Cell lysates were prepared in Laemmli electrophoresis sample buffer and analyzed by SDS-PAGE under reducing (100 mM 2-mercaptoethanol) or non-reducing conditions. Prestained protein markers (GIBCO) were used as reference. Protein concentrations were quantitated by the biuret assay (Bio-Rad, Melville, N.Y.), and by parallel Coomassie blue staining of SDS-PAGE gels. For western blotting samples were electrotransfered to PVDF (Xymotech Biosystems, Mt. Royal, QC), blocked overnight in TBST (0.05 M Tris base, 0.2 M NaCl, 0.5% Tween™-20, pH 7.6) containing 1% BSA (Sigma), and immunoblotted with the indicated primary mAbs. Secondary antibodies were either horseradish peroxidase (HRP) conjugated goat anti-rabbit IgG (HRP-GαR), or goat anti-mouse IgG (HRP-GαM) (Sigma). For detection the enhanced chemiluminescence (ECL) reagents (Amersham, Oakville, Ont.) were used following the manufacturer's instructions. Densitometric analysis was performed with a Masterscan Interpretive Densitometer CSPI™ and a Howtek Scanmaster™ (Scanalytics, Billerika, Mass.).

Binding, Competition, and Internalization Assays

MAb 5C3 was $^{125}$I-labeled by the Iodogen (Pierce) method (Harlow, E., Lane, D. (1988) *A Laboratory Manual*. Cold Spring Harbour Laboratory Publishing. Chapter 9:332–333) to a specific activity of 1.8 mCi/mg. $^{125}$I[5C3] was repurified from free $^{125}$I with Sephadex G25 columns (15×1 cm) to >96% trichloroacetic acid precipitable incorporation. Binding studies were performed with serial dilutions of $^{125}$I[5C3] on $0.5 \times 10^6$ E25 or 4-3.6 cells (and their respective controls NIH-3T3 and B104 cells) for 1 hour at 4° C. Cell-associated $^{125}$I[5C3] and free $^{125}$I[5C3] were counted after washing unbound ligand. Parallel $^{125}$I[NGF] (70 mCi/mg) (NEN-DuPont, Mississauga, Ont.) binding assays were performed as control. Competition of $^{125}$I[5C3] binding was done in binding assays in the presence of unlabeled mAb 5C3 (100-fold molar excess), or unlabeled NGF (500-fold molar excess).

Competition of $^{125}$I[NGF] binding was performed by first incubating cells with excess unlabeled mAb 5C3, NGF, mAb 87.92.6 or vehicle binding buffer for 30 min at 4° C. $^{125}$I[NGF] was then added to a final saturating concentration of ~1 nM, the mixtures incubated for an additional 45 min at 4° C., cells were washed and cell-associated 125I[NGF] were determined.

Based on the competition assays above, it was desirable to identify the mAb 5C3 receptor docking site which is presumed to be a functional or energy-favorable site where the ligand-binding causes receptor-mediated signals.

This view is supported by similar findings in the EPO receptor system (Wrighton et al., 1996, Science, 273:458) wherein a "docking hot spot" was found; and by our finding that mAb 5C3 and NGF block each other's binding.

The docking site of mAb 5C3 was identified within the juxtamembrane/IgG2 domain of human TrkA receptors.

The sequence is as follows:

change in the affinity of mAb 5C3 for TrkA receptors. Similar data was obtained measuring mAb 5C3 binding sites by FACScan analysis, where a decrease was observed after NGF treatment (Table 2).

TABLE 2

| mAb 5C3-induced Trka receptor internalization | | |
|---|---|---|
| TREATMENT | TEMP. (° C.) | % 5C3 STAINING |
| NGF (2 nM) | 4° C. | 83 ± 2.0 |
|  | 37° C. | 75 ± 3.6 |
| 5C3 (0.01 µg/ml) | 4° C. | 96 ± 9.0 |
|  | 37° C. | 77 ± 5.5 |

TrkA surface immunostaining was performed on 4-3.6 cells with mAb 5C3 after the indicated treatments, and measured by FACScan analysis. Data is presented as %

```
Gln Val Asn Val Ser Phe Pro Ala Ser Val Gln Leu His Thr Ala Val   (SEQ ID NO:9)
1            5                  10                  15

Glu Met His His Trp Ser Ile Pro Phe Ser Val Asp Gly Gln Pro Ala
             20                  25                  30

Pro Ser Leu Arg Trp Leu Phe Asn Gly Ser Val Leu Asn Glu Thr Ser
             35                  40                  45

Phe Ile Phe Thr Glu Phe Leu Glu Pro Ala Ala Asn Glu Thr Val Arg
    50                  55                  60

His Gly Cys Leu Arg Leu Asn Gln Pro Thr His Val Asn Asn Gly Asn
65                  70                       75                  80

Tyr Thr Leu Leu Ala Ala Asn Pro Phe Gly Gln Ala Ser Ala Ser Ile
             85                  90                  95

Met Ala Ala Phe Met Asp Asn Pro Phe Glu Phe Asn Pro Glu Asp Pro
             100                 105                 110

Ile Pro Asp Thr Asn Ser Thr Ser Gly Asp Pro Val Glu Lys Lys Asp
             115                 120                 125

Glu Thr Pro
    130
```

For receptor internalization studies cells were incubated with TrkA-binding agents (0.01 µg mAb 5C3; 2 nM NGF) or controls (mIgG; HBSS) for 20 min either at 37° C. (internalization permissive temperature) or at 40° C. (internalization non-premissive temperature). After washing, cells were processed for surface TrkA immunofluorescence with mAb 5C3 primary and FITC-GamIgG secondary as above, and analyzed by FACScan.

Binding Studies

Scatchard plot analysis of $^{125}$I[5C3] binding assays demonstrated that in the E25 cell surface there are ~250,000 5C3 binding sites/cell with a $K_d$ of 1.6 nM (FIG. 5), and in the 4-3.6 cell surface there are ~200,000 5C3 binding sites/cell with a $K_d$ of 3.0 nM.

Serial dilutions $^{125}$I[5C3] without competition (open triangles) were used in binding studies with a constant number of E25 cells. Binding was competed with molar excess of unlabeled NGF (filled circles) or mAb 5C3 (open squares). In 3 independent experiments the average $K_d$ of mAb 5C3 in E25 cells was 1.6 nM. Competition with NGF reduced the number of 5C3 binding sites in E25 cells but the affinity of mAb 5C3 was not affected.

No $^{125}$[5C3] binding was observed for parental NIH-3T3 or B104 cells. NGF competition reduced the number of 5C3 binding sites in E25 cells by 25%. However, NGF caused no staining±sem, with reference to control vehicle treatment (100%) as per the following formula:

(Treated sample staining−mIgG background staining)×100%
(maximum staining−mIgG background staining)

In the converse experiment, mAb 5C3 inhibited ~60% of $^{125}$I[NGF] binding to E25 cells. In these experiments background binding was assessed by blocking with 5 µM NGF (100% inhibition), and maximal binding was assessed with binding buffer vehicle only (0% inhibition) or by using irrelevant binding mAb 87.92.6 (Table 3).

TABLE 3

| MAb 5C3 blocks NGF binding to TrkA | |
|---|---|
| TREATMENT | % NGF BINDING |
| mAb 5C3 | 39.3 ± 7.4 |
| mAb 87.92.6 | 100 |
| NGF (5 µM) | 0 |

E25 cells expressing TrkA (but not p75 receptors) were incubated with $^{125}$I[NGF] in the presence of the indicated agents. $^{125}$I[NGF] binding after treatment with mAb 87.92.6 was identical to treatment with vehicle binding buffer. Assays were done 3 times in duplicate. Data is expressed as % binding±standard deviation (sd), where mAb 87.92.6 is maximum and 5 µM NGF is background binding as per the formula:

$$\frac{(test - background) * 100\%}{(maximum - background)}$$

Proliferation/survival Assays 5,000 cells/well in serum-free media (SFM) (GIBCO) supplemented with 0.1% BSA were added to 96 well plates (Falcon, Lincoln Park, N.J.) containing serial dilutions of NGF, mAb 5C3, control mAbs, mAb 5C3 $F_{ab}$ fragments, control mAb 192 $F_{ab}$ fragments or serum (final 5% FBS, normal growth conditions). Where indicated, $F_{abs}$ were externally cross-linked with goat anti-mouse $F_{ab}$ (G$\alpha$m$F_{ab}$, Sigma). Wells containing all culture conditions but no cells were used as blanks. The proliferative/survival profile of the cells was quantitated using the tetrazolium salt reagent (MTT, Sigma) 48–72 hours after plating as initially described by T. Mosmann (Hansen, M. B. et al.(1989) *Jour. Immunol. Meth.*, 119: 203–210). Optical density readings of MTT were done in an EIA Plate Reader Model 2550™ (Bio-Rad) at 600 nm with the blanks subtracted. Assays were repeated at least 5 times in quadruplicates.

Foci Formation Assays

15×10⁴ E25 cells were plated in a 25% serum-containing 0.35% soft agar mixture in the presence of either mIgG control (0.5 µg/ml), mAb 5C3 (0.5 µg/ml), or NGF (2 nM). Conditions were replenished every 3 days and foci were counted after two weeks.

Immunocytochemistry of Human Brain Tissues

Human brain tissue was obtained from six males (age 71.7±4.6) without signs of neurologic or psychiatric disorders. Tissue blocks were prepared (mean time post-mortem 16.2±3.5 hrs) and stored at −80° C. Twenty µm thick cryostat sections were fixed (4% paraformaldehyde, 0.1 M phosphate, pH 7.4; 1 hour at 4° C.), and rinsed in PBS for 1 hour at 4° C. Immunocytochemistry was performed using avidin-biotin complex (Vectastain Elite™ kit, Vector Labs) as described (Hsu, S-M. et al. (1981) *J. Histochem. Cytochem.*, 29: 577–580). Primary mAb 5C3 was used either as a 1:1000–1:4000 dilution of ascites or a 1:4 dilution of serum free-media culture supernatant. Where indicated, 0.5% nickel ammonium sulfate was used to amplify the signal in the DAB revelation step. Some sections were also stained with cresyl violet to facilitate the cytoarchitectural analysis. Negative controls were performed without primary antibody or with normal mouse IgG as primary and in all cases yielded no detectable immunolabeling.

Immunostaining in Normal Human Brain

MAb 5C3 was used to map TrkA protein expression by immunocytochemistry of normal adult human brains. The striatum, the basal forebrain and the brainstem exhibited the strongest immunostaining, whereas only weak staining could be detected in the cerebral cortex and hippocampal formation (FIG. 3).

FIGS. 3A and 3B illustrate low power photomicrographs of the nucleus basalis of Meynert showing large neurons (arrows) immunoreactive with mAb 5C3 (FIG. 3A) but lacking immunoreactivity with normal mouse IgG (FIG. 3B) in a consecutive section. Note in A that the labeled neuronal processes can often be followed (small arrows). Scale bar=50 µm.

FIGS. 3C, 3D, and 3E illustrate high power photomicrographs of TrkA-containing neurons in the nucleus basalis (FIG. 3C), the putamen (FIG. 3D), and the CA4 sub-field of the hippocampus (FIG. 3E). The perinuclear area displayed particular strong concentration of DAB precipitate (small arrows) often in granules. Labeled proximal processes could also be observed (arrows). n, nucleus. Scale bars=10 µm.

FIG. 3F illustrates in the pontine nuclei many weakly to strongly staining neurons (arrows) within the fiber network (small arrows) and around the non-labeled fiber bundles (FIG. 3F). Scale bar=20 µm.

FIG. 3G illustrates in the reticular formation of the brainstem numerous fibers (small arrows) constitute a network where some scattered neurons (arrow) are observed. Scale bar=20 µm.

FIG. 3H illustrates a photomicrograph of TrkA immunoreactivity in the frontal cerebral cortex showing weak labeling. A few neurons are weakly positive (arrows) with the staining residing mostly in puncta possibly corresponding to fibers (small arrows). Scale bar=10 µm.

All sectors of the basal nucleus contained large TrkA-positive neurons (FIGS. 3A and 3C), most of them in groups embedded in a dense network of overlapping stained processes (FIG. 3A). The cells had heterogeneous shapes, ranging from complex multipolar to fusiform.

In the basal ganglia TrkA was detected in distinct cellular compartments. The caudate nucleus, the nucleus accumbens and the putamen contained several immunoreactive cell bodies without apparent distinction in density, perikaryal staining and shape. FIG. 3D shows typical labeled multipolar neurons that displayed strong granular immunoreactivity around the nucleus and in proximal processes. Moreover, numerous puncta and varicose fiber fragments were observed in these areas. The globus pallidus and the claustrum were mostly negative except for varicose fibers. Similarly, the interstitial elements and fiber bundles did not contain reactive fibers whereas the internal capsule displayed some labeled punctas and fibers particularly near the putamen and caudate nucleus.

The hippocampal formation showed weak immunostaining located principally in scattered fibers and puncta in the stratum granulosum of the dentate gyrus, as well as in the strati oriens and pyramidal of the Ammon's horn. In addition, some weakly stained perikarya could be observed in the stratum pyramidal of the CA2 and CA3 sub-fields of the Ammon's Horn and in the hilus of the dentate gyrus (CA4 sub-field, FIG. 3E). The perikarya of these neurons was relatively large in size, of ovoid to pyramidal shape, and bearing one prominent apical and radial dendritic process. The immunoreactivity appeared like in other stained cell types of the brain as small granular patches of precipitate located principally near the nuclear envelope and in some cases within the cytoplasm (FIG. 3E).

Within the cerebral cortex, particularly in the frontal area, TrkA immunoreactivity appeared more discrete. At high magnification, immunoreactive puncta and fiber fragments without a particular pattern of distribution are observed in all layers, but the laminae III–VI appeared more stained than superficial ones (FIG. 3H). Occasional, weakly staining, medium-sized perikarya were observed in layer IV (FIG. 3H).

In the brainstem TrkA staining is also detected. The pontine nuclei contained numerous immunoreactive medium sized globular perikarya and fibers between the pontocerebellar fibers (FIG. 3F). The reticular formation also displayed strong immunoreactivity for TrkA principally located in fiber networks (FIG. 3G). Some large neurons of bipolar or multipolar shape are also stained. No TrkA immunostaining was observed in the cerebellum.

Functional Agonism of mAb 5C3

Several functional assays of NGF bioactivity were used to test the agonistic potential of mAb 5C3.

Figure 5:
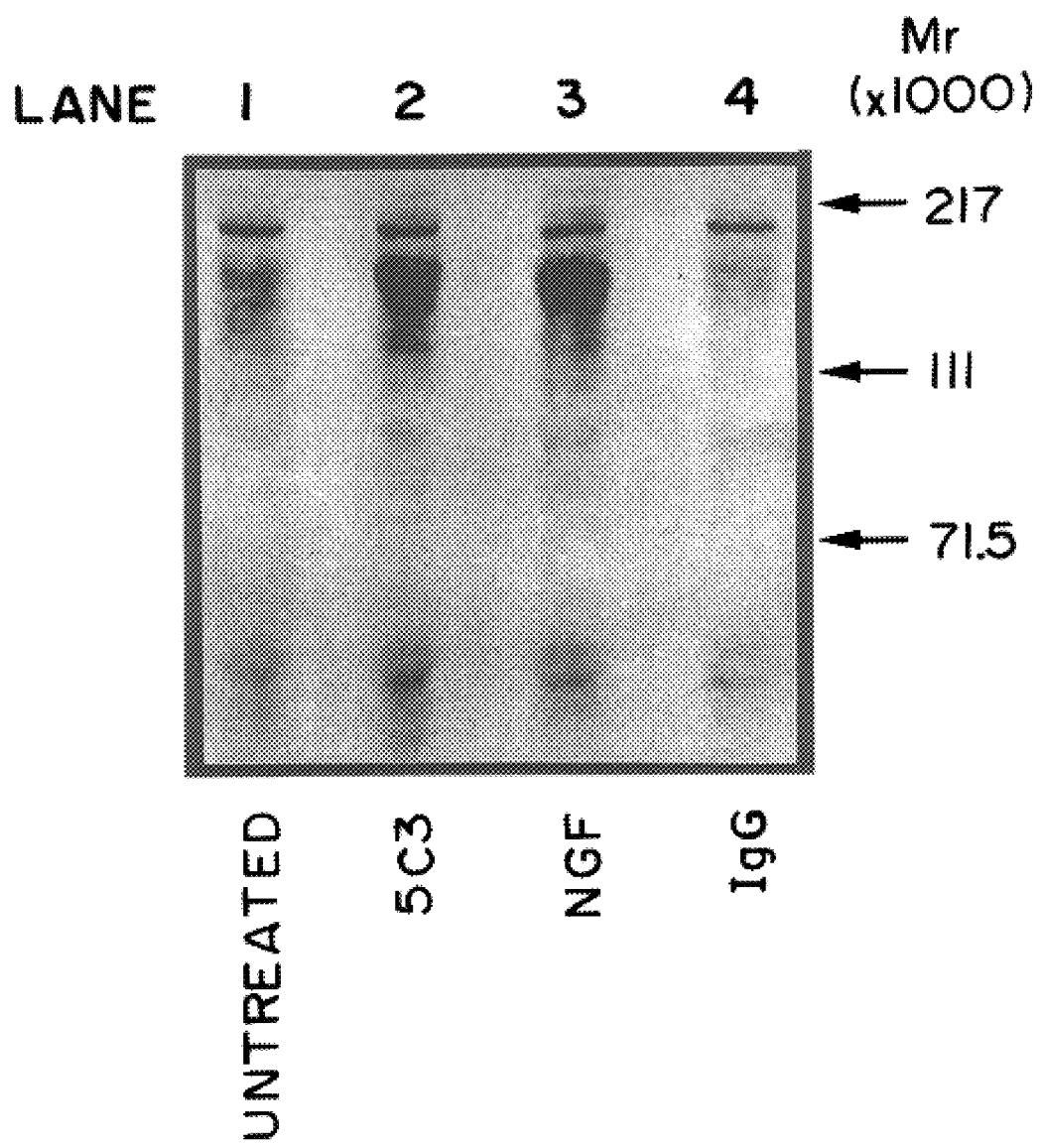
FIG. 5 illustrates 5C3 binding studies and Scatchard plot analysis.

Receptor Internalization 4-3.6 cells were treated with TrkA ligands at internalization permissive temperatures (37° C.) or at non-permissive temperatures (4° C.) (Table 2). NGF treatment reduced the % staining of mAb 5C3 to surface TrkA at both temperatures. Loss of surface 5C3 binding sites suggest direct blocking by NGF (FIG. 5). In contrast, mAb 5C3 treatment reduced the number of surface 5C3 binding sites only at 37° C. This is likely due to receptor internalization, which does not occur efficiently at 4° C. Treatment with mIgG or binding buffer control did not reduce the number of surface 5C3 binding sites at either temperature. Similar data was obtained with E25 cells.

Receptor Phosphorylation

Anti-phosphotyrosine western blots of E25 or 4-3.6 whole cell detergent extracts revealed that TrkA phosphotyrosinylation (PY) increased significantly over basal levels after short treatment with mAb 5C3 or with NGF (FIG. 4).

E25 cells were untreated (lane 1) or treated with mAb 5C3 (lane 2), NGF (lane 3), or mIgG (lane 4) for 15 min. at 37° C. Whole cell lysates were resolved in a 8% SDS-PAGE under reducing conditions and immunoblotted with anti-phosphotyrosine mAb 4G10. A parallel gel under non-reducing conditions immunoblotted with mAb 5C3 (not shown) controlled for Mr and equal loading of TrkA on all samples.

Densitometric analysis of several blots from E25 and 4-3.6 cells is presented in Table 4.

TABLE 4

TrkA tyrosine phosphorylation by mAb 5C3

| TREATMENT | E25 cells | 4–3.6 cells |
| --- | --- | --- |
| mAb 5C3 | 2.7 ± 0.6 | 3.4 ± 1.5 |
| NGF | 6.5 ± 1.3 | 3.8 ± 0.8 |

E25 or 4-3.6 cells were untreated or treated with saturating concentrations of mAb 5C3 or NGF for 15 min. at 37° C. Whole cell lysates, or anti-PY immunoprecipitates were resolved by SDS-PAGE under reducing conditions, western transferred, immunoblotted with anti-phosphotyrosine ($\alpha$PY) mAb 4G10, and developed using ECL techniques. Optical density (O.D.) readings were taken from X-ray films with film backgrounds subtracted (see Materials and Methods). Data is presented as fold increase in PY of TrkA with respect to untreated cells±sd. n=3.

Other proteins evidence increased PY, including ~95 kDa and ~60 kDa proteins, and the p85 subunit of PI-3 kinase (~2.5-fold increase). We have estimated that <10% of all p85 material was tyrosine phosphorylated upon ligation of TrkA.

Increased Cellular Transformation

NGF treatment causes the transformation and an increase in anchorage-independent growth of TrkA-expressing E25 cells. MAb 5C3 caused a ~2-fold increase in the number and the size of foci as compared with mIgG treated cells (Table 5).

TABLE 5

MAb 5C3-induced anchorage-independent growth

| TREATMENT | AVERAGE NUMBER OF FOCI[a] | TYPICAL CELLS/FOCI[a] | FOLD INCREASE IN FOCI[b] |
| --- | --- | --- | --- |
| mIgG | 416 ± 45 | ~24 | 1 ± 0.11 |
| mAb 5C3 | 806 ± 178 | >48 | 1.9 ± 0.22 |
| NGF | 676 ± 51 | ~24 | 1.6 ± 0.08 |

E25 cells were cultured in soft agar in the presence of the indicated agents for 2 weeks. [a]Average number and typical size of foci±sd are shown. [b]Fold increase in foci was calculated with respect to mIgG treated cells (no increase). n=2.

No change in the number or size of foci was observed in wild type NIH-3T3 cells upon mAb 5C3 treatment.

Protection from Cell Death

Figure 6:
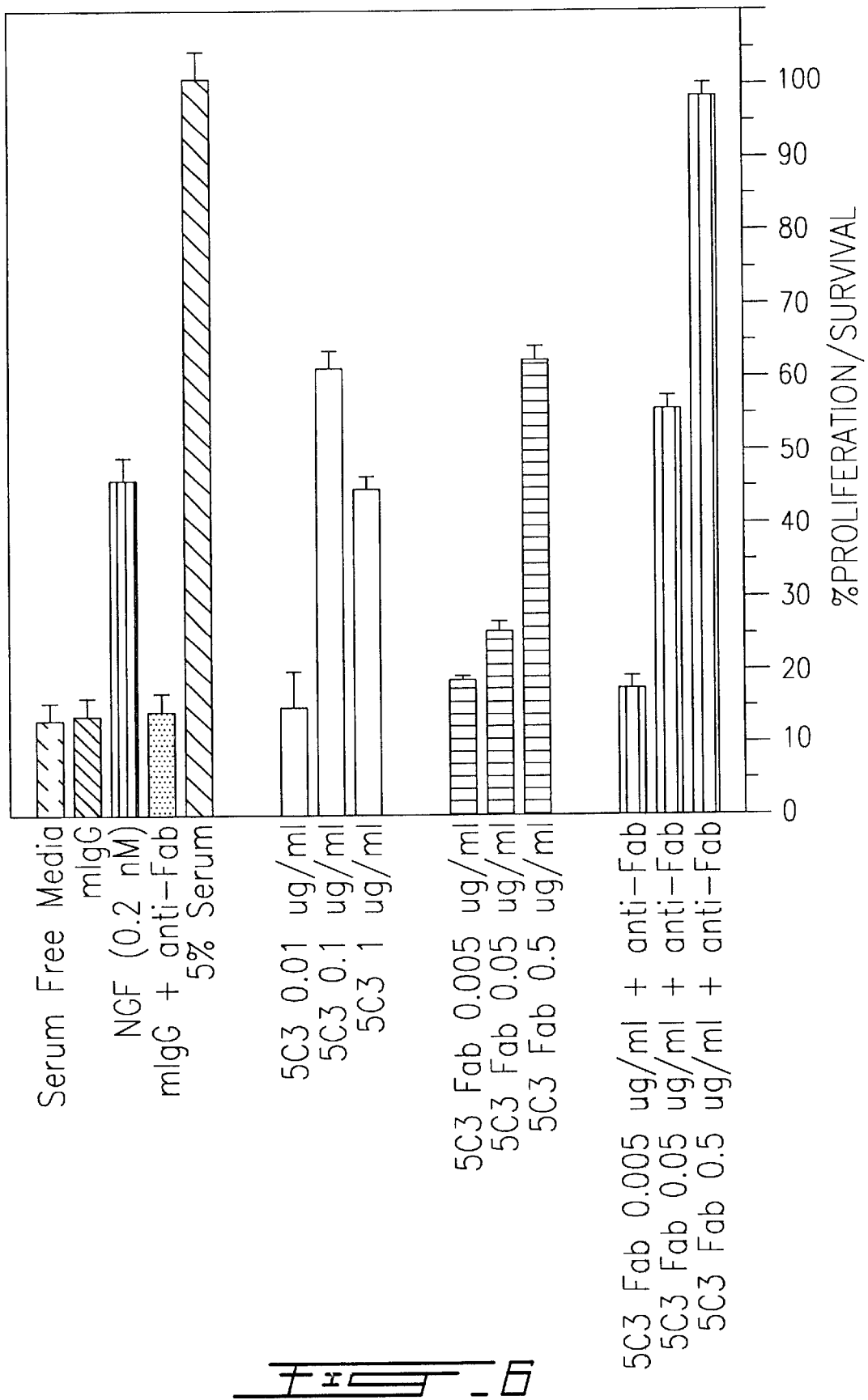
FIG. 6 illustrates the protection from apoptotic death by 5C3 and 5C3 Fabs.
Figure 8:
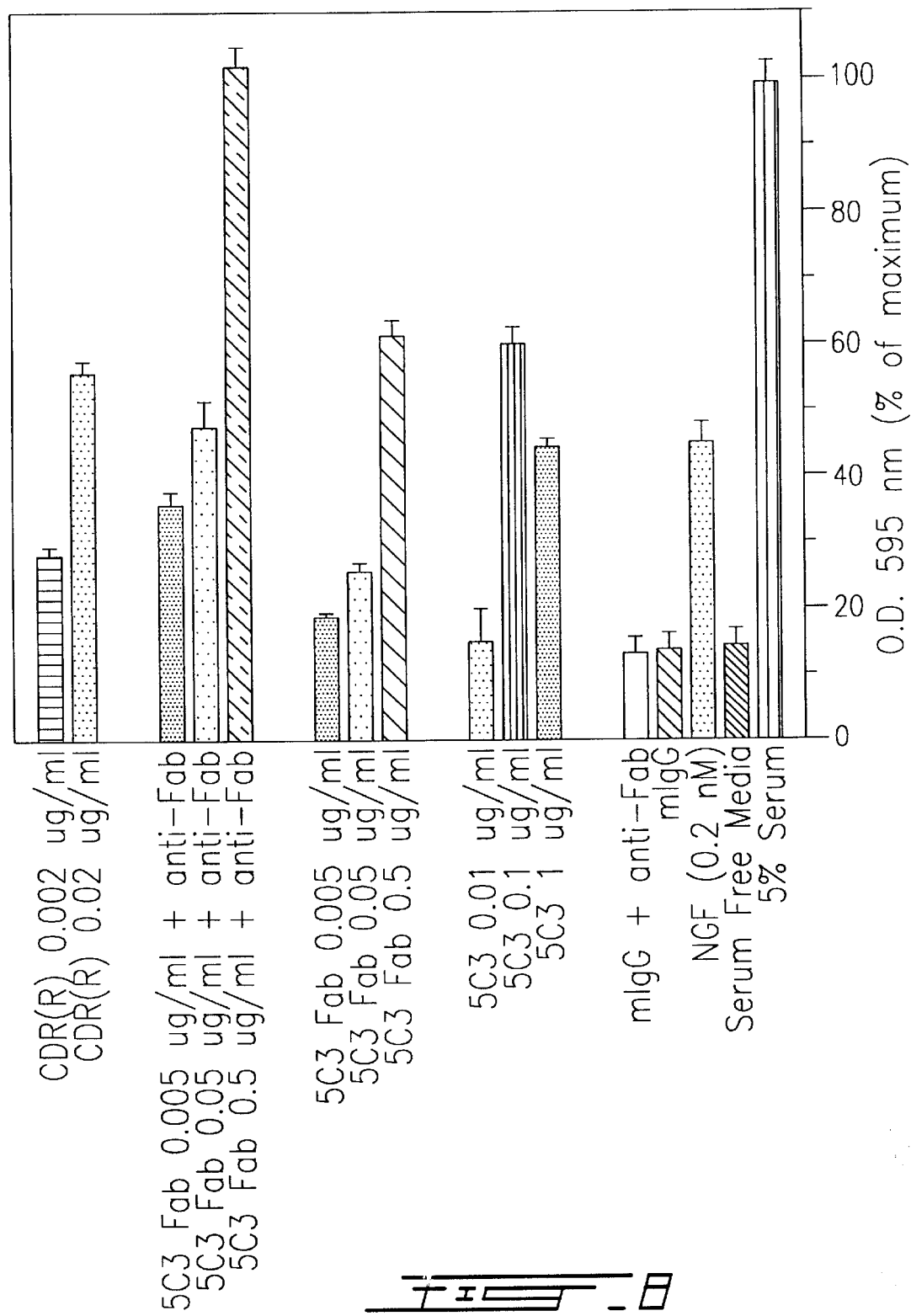
FIG. 8 illustrates the survival of TrkA-expressing cells in serum-free media by 5C3 and derivatives.

Agonistic ligands of TrkA protect receptor-expressing cells from death in serum-free media (SFM). Both NGF and mAb 5C3 and 5C3 fragments or derivatives increased the number of surviving/proliferating E25 fibroblastoid cells (FIG. 6) and 4-3.6 cells (FIG. 8).

Cells were cultured in Serum Free Media supplemented with the indicated conditions for 2–3 days, followed by the MTT assay. Similar data was obtained with neuronal 4-3.6 cells (FIG. 8). The % proliferation/survival was determined by standardizing serum containing wells to 100% with the use of the following formula:

$$\frac{(\text{O.D. of test}) \times 100\%}{(\text{O.D. of serum})}$$

Equivalent protection was also afforded by TrkA ligands to neuronal 4-3.6 cells. In most experiments mAtb 5C3 protection is dose-dependent, although high dose antibody inhibition is sometimes seen (e.g. 1 mg/ml of mAb 5C3).

To ascertain whether cell death is apoptotic, DNA was prepared from serum-free cultured cells which showed a typical apoptotic fragmentation ladder. The DNA ladder was not seen in preparations from cells cultured in the presence of mAb 5C3 or NGF.

Controls demonstrated the functional specificity of mAb 5C3. First, neither NGF nor mAb 5C3 protected wild type NIH-3T3 cells. Second, PC12 cells were not protected by mAb 5C3 but were protected by NGF. Third, irrelevant mIgG, G$\alpha$mF$_{ab}$, or mAb 192 did not protect E25 cells (FIG. 6), or NIH-3T3 cells, or 4-3.6 cells (FIG. 8).

Functional Agonism of Monomeric 5C3 Fabs

Monovalent agents that bind TrkA behave as competitive antagonists (Clary, D. O. et al. (1994) *Mol. Biol. Cell.*, 5: 549–563; LeSauteur, L. et al.(1995) *J. Biol. Chem.*, 270:6564–6569) likely because they can not induce receptor dimerization. Therefore, it would be expected that monomeric 5C3 F$_{abs}$ would be monovalent and not be able to mediate agonistic function.

MAb 5C3 F$_{abs}$ afforded protection from apoptotic death to E25 cells (FIG. 6) and 4-3.6 cells in serum-free media. Moreover, anti-phosphotyrosine western blots revealed that cells treated with 5C3 F$_{abs}$ had increased TrkA tyrosine phosphorylation similar to increases obtained with whole mAb 5C3.

Monomeric 5C3 F$_{ab}$ protection was dose-dependent. However, equivalent or better protective effects were achieved when F$_{abs}$ were externally cross-linked with G$\alpha$mF$_{ab}$ antibodies. Specificity controls included those described in the previous section for whole mAb 5C3, plus 192 $F_{abs}$ which had no protective activity in E25 cells.

DISCUSSION

The availability of antibodies against p140 TrkA and p75 has allowed the study of these NGF receptors. The mAb 5C3 reported herein is specific for human TrkA, functions in FACScan immunofluorescence analysis, immunoprecipitation, western blot analysis, and immunocytochemistry. Moreover, mAb 5C3 is a structural and functional mimic of NGF.

Aberrant expression of trkA mRNA and NGF responsiveness have been correlated with neurodegenerative disorders and neoplastic malignancy. Hence, TrkA-binding agents will be useful clinical tools in diagnosis, prognosis and perhaps treatment of these diseases. Indeed, mAb 5C3 binding is a positive prognostic marker for certain human neoplasias.

TABLE 6

TrkA expression in neuroblastoma

| Neuroblastomas* | Number | Positive | Mixed | Negative |
|---|---|---|---|---|
| Group 1 | 60 | 38 | 17 | 5 |
| Group 2 | 53 | 13 | 5 | 35 |

*15 samples repeated after chemotherapy, at the time of second surgery or recurrence: 5C3 staining patterns remained unchanged in 14 tumors; 1 negative tumor subsequently positive post chemotherapy in regions of maturing elements.

TABLE 7

TrkA expression in other malignant tumors

| Malignant tumor | N = 42 | TrkA-Pos |
|---|---|---|
| Central nervous system tumors | 6 | 0 |
| Rhabdomyosarcomas | 5 | 0 |
| Primitive neuroectodermal tumors | 6 | 0 |
| Ewing's sarcomas | 2 | 0 |
| Wilm's tumors | 6 | 1 |
| Osteosarcomas | 4 | 0 |
| Melanomas | 5 | 0 |
| Breast carcinomas | 5 | 0 |
| Lung carcinomas | 3 | 0 |

TABLE 8

TrkA detection by immunocytochemistry, RT-PCR and western blot

| IMMUNOCYTO. | N | RT-PCR Pos | N | West. Pos |
|---|---|---|---|---|
| Group 1 | | | | |
| 5C3 Pos | 15 | 15 | 2 | 2 |
| 5C3 Neg | 4 | 4 | 2 | 1 |
| 5C3 Mixed | 1 | 1 | 10 | 10 |
| Group 2 | | | | |
| 5C3 Pos | 11 | 11 | 11 | 11 |
| 5C3 Neg | 11 | 4 | 9 | 5 |
| 5C3 Mixed | 2 | 2 | 0 | 0 |

MAb 5C3 recognizes a disulfide-stabilized domain of TrkA and an extracellular epitope with these characteristics appears to be the NGF docking site. Cross-blocking studies indicated that mAb 5C3 and NGF can reciprocally block each other's binding to TrkA, further suggesting that the docking site of 5C3 may be similar to NGF. In addition, sequence comparison of both ligands revealed interesting homology between CDRs of mAb 5C3 and the variable turn regions of NGF. Since most CDRs are β-turns (Sibanda, B. L. et al. (1989) *J. Mol. Biol.*, 206: 759–777) and coincidentally the NGF structures that bind TrkA may also be β-turns (LeSauteur, L. et al.(1995) *J. Biol. Chem.*, 270:6564–6569) we hypothesized that both mAb 5C3 and NGF bind to the same site on human TrkA, and cross-blocking is likely to be the result of direct competition rather than steric hindrance.

Interestingly, mAb 5C3 was more efficient at blocking NGF binding than vice versa. Only ~25% of the mAb 5C3 binding sites on E25 cells were blocked by saturating doses of NGF. This data suggest that not all TrkA receptors in these cell lines bind NGF. It is unlikely that affinity considerations can account for these observations, as both ligands have roughly comparable $K_d$ for TrkA (mAb 5C3 $K_d$ ~2 nM versus NGF $K_d$ 0.7 nM (Jing, S. et al. (1992) *Neuron*, 9: 1067–1079)) and the affinity of mAb 5C3 was unchanged in the presence of NGF.

Three non-exclusive possibilities can account for these observations: (i) TrkA receptors exist at equilibrium where ~25% are in an NGF binding conformation (e.g. dimers) and the rest are in a non-NGF binding conformation; (ii) specific post-translational modifications of TrkA receptors allow for NGF binding (iii) expression of other membrane proteins (e.g. p75 or unknown proteins) induce or favor the NGF binding conformation of TrkA. These hypotheses can be addressed by biochemical analysis after differential affinity purification of TrkA with mAb 5C3 versus NGF and by further binding studies in neuronal and fibroblastoid-cells expressing different receptors.

Absence of mAb 5C3 binding to rat TrkA is intriguing. Binding by mAb 5C3 to rat TrkA was expected because of the homology between mAb 5C3 CDRs and the variable loops of NGF, particularly since NGF from one species does bind to TrkAs from other species. MAb 5C3 is a binding and structural mimic of NGF, with enhanced human receptor specificity. Remodeling and mutating of the CDRs of mAb 5C3 will yield a pan-TrkA binding mAb. Further, analysis of the epitope of mAb 5C3 on TrkA revealed differences in the docking site of human and rat TrkAs. This information will be useful in screening receptor-binding analogs.

To test functional mimicry by mAb 5C3, NGF bioassays were performed using trkA transfected fibroblast and neuronal cells. Functional mimicry by mAb 5C3 included TrkA internalization, TrkA tyrosine phosphorylation, PI-3 kinase phosphorylation, increased anchorage-independent growth and proliferation/survival of cells in serum-free media. By these criteria mAb 5C3 is agonistic.

Increased TrkA receptor turnover or internalization is induced by NGF binding. MAb 5C3 increased the internalization of TrkA, as measured by loss of cell surface receptors. These results are consistent with data which showed that E25 cells internalize $^{125}$I[NGF] within seconds upon shifting from 40° C. to 37° C. (Jing, S. et al. (1992) *Neuron*, 9: 1067–1079) and that this process does not require p75 receptors. Thus, artificial ligands of TrkA can induce receptor internalization and could be useful in delivering toxic agents to the cytoplasma of TrkA-expressing tumors.

NGF ligation of TrkA causes receptor activation and autophosphorylation. MAb 5C3 induced TrkA tyrosine phosphorylation to a similar degree. Agonism in the absence of NGF suggests that TrkA dimerization and/or internalization are the required signaling event, rather than the formation of NGF-TrkA complexes. However, we can not rule out that mAb 5C3-TrkA is the functional signal transducing complex.

Ligand-induced tyrosine phosphorylation of the intracellular domain of TrkA allows for the recruitment of substrates and the activation of cytosolic proteins and nuclear oncoproteins. MAb 5C3 induces the tyrosine phosphorylation of proteins of $M_r$ 60, 85 and 95 kDa. The 85 kDa protein was identified as PI-3 kinase, whose activation correlates with the actions of growth factors and oncogenes.

NGF stimulates neuronal survival and differentiation, and the proliferation of non-neuronal cells. NGF-activated TrkA induces transformation and morphological changes in fibroblast cells. MAb 5C3 caused similar increases in anchorage-independent growth and foci formation in soft agar. Thus, mAb 5C3 can positively modulate the growth of TrkA-expressing cells. Interestingly, the size of the mAb 5C3-induced foci were larger on average than NGF-induced foci.

TrkA-expressing neuronal 4-3.6 cells or fibroblastoid E25 cells undergo apoptotic death in serum free media but can be rescued by NGF or mAb 5C3. Synergy between the two ligands occurred when combined at suboptimal doses, as would be expected if mAb 5C3 bound and activated unoccupied TrkA receptors. Furthermore, morphological changes and increased attachment to plastic were observed in both the NGF and 5C3 treated cells.

Monomeric 5C3 $F_{abs}$ protected E25 and 4-3.6 cells from apoptotic death. When $F_{abs}$ were externally cross-linked using anti-$F_{ab}$ antibodies, a heightened response occurred. Since growth factor receptor activation requires bivalent binding, the monomeric 5C3 $F_{abs}$ must have retained the ability to induce TrkA oligomerization. This could be explained in the following 3 ways: (i) $F_{abs}$ are relatively large molecules capable of aggregation; (ii) 5C3 $F_{ab}$ binding, could cause conformational changes in TrkA which induce receptor-receptor interactions; and (iii) monomeric 5C3 $F_{abs}$ bind to two receptor molecules in a bivalent manner. The last possibility could occur by two CDRs binding to two different TrkAs. Homology of mAb 5C3 CDRs to NGF turn regions, and experiments using small recombinant antibody analogs support the last explanation.

MAb 5C3 is the first report of an agonistic anti-neurotrophin receptor mAb and will be useful in studies of TrkA biology and for drug development. Antineoplastic effects with mAb 5C3 may be achieved either through terminal differentiation, antibody-dependent cell cytotoxicity, or by the delivery of toxins or radionuclides. Furthermore, the structure of this mAb may be useful in designing peptidic and non-peptidic TrkA binding agents (Saragovi, H. U. et al. (1991) *Science*, 253: 792–795). Small non-peptide agonists of TrkA should be useful pharmacological agents for the treatment of neurodegenerative diseases.

The present invention will be more readily understood by referring to the following examples which are given to illustrate the invention rather than to limit its scope.

EXAMPLE I

Preliminary Study of the Effect of mAb 5C3 in Tumor Growth

Figure 10:
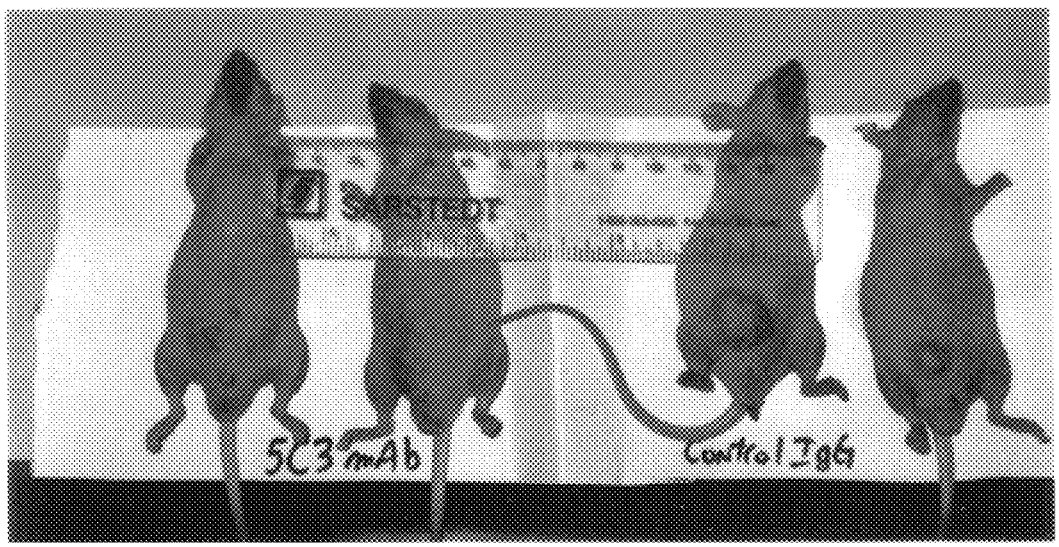
FIG. 10 illustrates Mab5C3 prevents TrkA-expressing tumor growth in vivo.

Nude mice were injected subcutaneously (right abdominal side) with 2×10⁶ human TrkA expressing tumor cells. Two days post-injections tumors in all mice had begun to form. Mice were randomized prior to treatment. A total of four intraperitoneal injections of 100 micrograms each on the left side were then administered over a 12 day period with control mouse IgG or mAb 5C3 (FIG. 10).

The mAb 5C3 dramatically reduced the primary tumor weight with no observable metastatic invasion. A small fibrotic mass was localized at the site of injection in mAb 5C3 treated mice. In contrast, IgG treated mice had large, vascularized tumor masses, which metastasized to the liver, peritoneum gut and spleen. All animals had similar body weights (~30 grams).

TABLE 9

| TREATMENT | PRIMARY TUMOR WEIGHT (mg) | METASTASIS WEIGHT (mg) |
| --- | --- | --- |
| 5C3 mAb | 50 ± 20 (fibrotic) | NONE |
| mouse IgG | 800 ± 250 | 350 ± 20 |

EXAMPLE II

Figure 7:
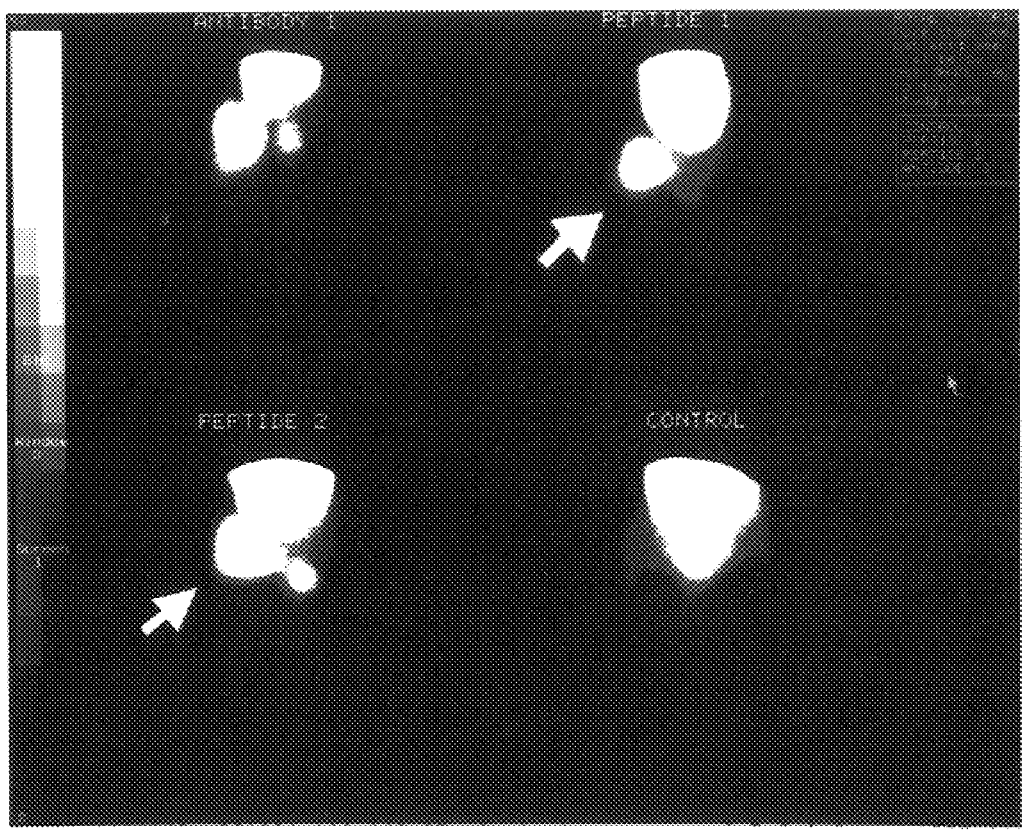
FIG. 7 illustrates nuclear imaging of tumors in vivo with 5C3.

The Use of Mab 5C3 and Its Derivatives for the Diagnosis, Prognosis and Localization of Tumors The in vivo targeting efficacy of agents that bind the NGF receptor p140 TrkA was evaluated. Nuclear imaging studies were done after the injection of $^{99m}$Tc-labeled compounds in nude mice bearing tumors. Kinetics of tumor targeting, blood clearance, and bioavailability were studied. Tumors that do not express TrkA were not targeted, demonstrating the specificity in vivo. This biodistribution study demonstrates that receptor-specific molecule analogs may be useful and may be effective agents for the detection, diagnosis, and possible treatment of neoplasias involving overexpressed oncogenic receptors such as TrkA (FIG. 7).

TABLE 10

Biodistribution of $^{99m}$Tc-[TrkA ligands] in mice.

| | | $^{99m}$Tc-[5C3] | |
| --- | --- | --- | --- |
| | Ligand | % id/g | T/nT |
| 1 | tumor | 1.25 | 1 |
| 2 | blood | 0.1 | 13 |
| 3 | muscle | 0.06 | 20 |
| 4 | heart | 0.10 | 13 |
| 5 | lung | 0.17 | 7.30 |
| 6 | liver | 0.61 | 2.10 |
| 7 | spleen | 0.13 | 9.42 |
| 8 | kidney | 1.48 | 0.9 |
| 9 | large bowel | 2.2 | 0.7 |

EXAMPLE III

5C3 Protein Sequence

Kappa light chain

DILQTQSPAILSASPGEKVTMTCRASSS-
VSYMHWYQQKPGSSPKPWIYATSNLAS-
GVPARFSGSGSGTSYSLTISRVE-
AEDAATYYCQQWSSNPLTFGAGTKLEI    (SEQ ID NO:1)

Heavy chain (IgG2a)

VQLQESGTVLARPGASVKMSCKASGYT-
FTSYWMHWVKQRPGQGLEWIGAIYPGDS-
DTSYNQKFKGEAKLTAVTST-
STAYMELSSLTNEDSAVYYCTLYGNYESYYA
MDYWGQGILSHRLL    (SEQ ID:2)

Complementarity Determining regions (according to Kabat, *Sequences of Proteins of Immunological Interest*, 4th ed. Bethesda, Md, U.S. Dept. of Health and Human Services. Public Health, NIH 1987)

Kappa variable light chain

| | |
|---|---|
| VL CDR1:RASSSVSYMH | (SEQ ID NO:3) |
| VL CDR2:ATSNLAS | (SEQ ID,NO:4) |
| VL CDR3:QQWSSNPLT | (SEQ ID NO:5) |

Heavy chain variable (IgG2a)

| | |
|---|---|
| VH CDR1:SYWMH | (SEQ ID NO:6) |
| VH CDR2:AIYPGDSDTSYNQKFKG | (SEQ ID NO:7) |
| VH CDR3:YGNYESYYAMDY | (SEQ ID NO:8) |

Antibodies have 6 complementarity determining regions (CDRs) that combine in specific ways to create direct contacts with their antigen. Molecular cloning, recombination, mutagenesis and modeling studies of mAb 5C3 variable region indicated that 3 or less of its CDRs are relevant for binding TrkA. These were named CDR1, CDR2, and CDR3. Region CDR1 is connected to CDR2 by a 15 amino acid linker; CDR2 is connected to CDR3 by a 30 amino acid linker. Their secondary structures have been analyzed.

The variable domains of mAb 5C3 heavy (VH) and light (LH) chains were cloned and sequenced. The predicted variable domain amino acid sequences are shown above.

The hypervariable complementarity determining regions (CDRs) were resolved according to Kabat (*Sequences of Proteins of Immunological Interest*, 4th ed. Bethesda, Md., U.S. Dept. of Health and Human Services. Public Health, NIH 1987).

An example of the model of the structure of the CDRs (Insight II™, Biosym, Calif.) within the backbone of the variable domains is shown in FIG. 11.

EXAMPLE IV

MAb 5C3 and Derivatives: Structural and Functional Mimics of NGF

Several criteria indicate that mAb 5C3 is a TrkA agonist. Previous functional studies in vitro demonstrated that mAb 5C3 can: (i) induce tyrosine phosphorylation of TrkA, and PI3-kinase; (ii) increase transformation of TrkA-expressing fibroblasts. Shown above are also experiments where the 5C3 and its derivatives protect cells from apoptotic death in serum-free media to the same degree as NGF does. Monovalent Fabs of 5C3 obtained after papain digestion are also agonistic, especially when externally cross-linked by anti-Fabs. A smaller fragment of mAb 5C3 called CDR(R) also protects cells from apoptosis (FIG. 8).

Assays with recombinant CDRs and CDR-like synthetic polypeptides demonstrated they had agonistic bioactivies similar to intact mAb 5C3. Consequently a 6 kDa recombinant molecule "CDR(R)" (for recombinant CDR) was developed as a replacement for mAb 5C3; it is approximately five times smaller than the 25 kDa NGF molecule and is still agonistic. CDR(R) is composed of 3 selected CDRs (out of 6 possible ones) linked by long spacer regions. Preliminary studies have suggested that actually only 2 of the 3 CDRs are relevant for binding to TrkA. Further, it is expected that even smaller fragments can be designed, e.g. upon removal of the linker regions.

4-3.6 cells transfected with human TrkA were cultured in serum-free-media (SFM) to induce apoptosis (FIG. 8). The indicated agents were added to the cells and cell viability was measured after 48–72 h by the MTT assay. Proliferation was standardized to normal growth conditions (5% serum). NGF, mAb 5C3, 5C3 Fabs, and CDR(R) (recombinant 5C3 CDR analog) protect from apoptosis, but mouse IgG (control) does not.

EXAMPLE V

Use of Mab 5C3

The mAb 5C3 of the present invention and its derivatives induce differentiation/neuritogenesis of human TrkA-expressing cells. PC12 cells (expressing rat TrkA) and PC12 cells transfected with and expressing human trkA cDNA were cultured with various TrkA binding agents or controls (FIG. 9) as indicated NGF caused the differentiation of wild type PC12 and PC12 transfectants, whereas SC3 and CDR (R) only induced differentiation of PC12 transfectants. Ligand doses are as shown in FIG. 8.

Further modifications of CDR(R) resulted in agents that support cell survival but not neuritogenesis.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

---

We claim:

1. A monoclonal antibody comprising SEQ ID NOS: 3, 4, 5, 6, 7, and 8.

2. A method of in vitro screening for an agent which is capable of activating Trka receptor, which comprises combining an antibody of claim 1 comprising SEQ ID NOS: 3, 4, 5, 6, 7, and 8 with TrkA receptor and a candidate agent and detecting reduced binding of said antibody to Trk A receptor, wherein reduced binding is indicative of binding to TrkA receptor by said candidate agent, indicating that said agent is capable of binding to TrkA receptor and thereby activating TrkA receptor.

3. A monoclonal antibody of claim 1, said antibody or an antigen binding fragment thereof capable of activating TrkA receptor, said antibody or antigen binding fragment thereof being raised against human TrkA receptor and binding specifically to TrkA receptor under physiological conditions, wherein said binding to said receptor activates the TrkA receptor.

4. A monoclonal antibody of claim 1, said antibody or antigen binding fragment thereof being raised against human TrkA receptor and specifically binding to TrkA receptor or to the IgG2 domain of TrkA receptor under physiological conditions, and wherein said binding to said domain activates TrkA receptor.

5. A monoclonal antibody of claim 1 or an antigen binding fragment thereof raised against human TrkA receptor and binding specifically to TrKA receptor under physiological conditions, and wherein said binding to said receptor activates TrkA receptor.

* * * * *

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
       (A) LENGTH: 105 amino acids
       (B) TYPE: amino acid
       (C) STRANDEDNESS:
       (D) TOPOLOGY: linear (ii) MOLECULE TYPE: protein (xi) SEQUENCE DESCRIPTION: SEQ ID NO: 1:

```
Asp Ile Leu Gln Thr Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
                20                  25                  30

His Trp Tyr Gln Gln Lys Pro Gly Ser Ser Pro Lys Pro Trp Ile Tyr
            35                  40                  45

Ala Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Ile
                100             105
```

(2) INFORMATION FOR SEQ ID NO: 2:

(i) SEQUENCE CHARACTERISTICS:
        (A) LENGTH: 120 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 2:

```
Val Gln Leu Gln Glu Ser Gly Thr Val Leu Ala Arg Pro Gly Ala Ser
1               5                   10                  15

Val Lys Met Ser Cys Lys Ala Ser Gly Tyr Thr Phe Thr Ser Tyr Trp
                20                  25                  30

Met His Trp Val Lys Gln Arg Pro Gly Gln Gly Leu Glu Trp Ile Gly
            35                  40                  45

Ala Ile Tyr Pro Gly Asp Ser Asp Thr Ser Tyr Asn Gln Lys Phe Lys
        50                  55                  60

Gly Glu Ala Lys Leu Thr Ala Val Thr Ser Thr Ser Thr Ala Tyr Met
65                  70                  75                  80

Glu Leu Ser Ser Leu Thr Asn Glu Asp Ser Ala Val Tyr Tyr Cys Thr
                85                  90                  95

Leu Tyr Gly Asn Tyr Glu Ser Tyr Tyr Ala Met Asp Tyr Trp Gly Gln
                100             105             110

Gly Ile Leu Ser His Arg Leu Leu
            115             120
```

(2) INFORMATION FOR SEQ ID NO: 3:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 3:

```
Arg Ala Ser Ser Ser Val Ser Tyr Met His
1               5                   10
```

(2) INFORMATION FOR SEQ ID NO: 4:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 4:

Ala Thr Ser Asn Leu Ala Ser
1               5

(2) INFORMATION FOR SEQ ID NO: 5:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 5:

Gln Gln Trp Ser Ser Asn Pro Leu Thr
1               5

(2) INFORMATION FOR SEQ ID NO: 6:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 6:

Ser Tyr Trp Met His
1               5

(2) INFORMATION FOR SEQ ID NO: 7:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 7:

Ala Ile Tyr Pro Gly Asp Ser Asp Thr Ser Tyr Asn Gln Lys Phe Lys
1               5                   10                  15
Gly (2) INFORMATION FOR SEQ ID NO: 8:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 8:

```
Tyr Gly Asn Tyr Glu Ser Tyr Tyr Ala Met Asp Tyr
1               5                   10

(2) INFORMATION FOR SEQ ID NO: 9:

(i) SEQUENCE CHARACTERISTICS:
        (A) LENGTH: 131 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 9:

Gln Val Asn Val Ser Phe Pro Ala Ser Val Gln Leu His Thr Ala Val
1               5                   10                  15

Glu Met His His Trp Ser Ile Pro Phe Ser Val Asp Gly Gln Pro Ala
            20                  25                  30

Pro Ser Leu Arg Trp Leu Phe Asn Gly Ser Val Leu Asn Glu Thr Ser
            35                  40                  45

Phe Ile Phe Thr Glu Phe Leu Glu Pro Ala Ala Asn Glu Thr Val Arg
        50                  55                  60

His Gly Cys Leu Arg Leu Asn Gln Pro Thr His Val Asn Asn Gly Asn
65                  70                  75                  80

Tyr Thr Leu Leu Ala Ala Asn Pro Phe Gly Gln Ala Ser Ala Ser Ile
                85                  90                  95

Met Ala Ala Phe Met Asp Asn Pro Phe Glu Phe Asn Pro Glu Asp Pro
            100                 105                 110

Ile Pro Asp Thr Asn Ser Thr Ser Gly Asp Pro Val Glu Lys Lys Asp
            115                 120                 125

Glu Thr Pro
    130
```